United States Patent
Casellini et al.

(10) Patent No.: US 6,220,862 B1
(45) Date of Patent: Apr. 24, 2001

(54) STRATIFIED MATERIALS USED IN DENTAL PROSTHESES

(75) Inventors: Fernando Casellini, Kornplatz 2, CH-7002 Chur; Renzo Casellini, Chur, both of (CH)

(73) Assignee: Fernando Casellini, Chur (CH)

( * ) Notice: Subject to any disclaimer, the term of this patent is extended or adjusted under 35 U.S.C. 154(b) by 0 days.

(21) Appl. No.: 09/297,772

(22) PCT Filed: Nov. 6, 1997

(86) PCT No.: PCT/EP97/06139

§ 371 Date: Aug. 13, 1999

§ 102(e) Date: Aug. 13, 1999

(87) PCT Pub. No.: WO98/19621

PCT Pub. Date: May 14, 1998

(30) Foreign Application Priority Data

Nov. 7, 1996 (CH) .................................................. 2748/96

(51) Int. Cl.⁷ .................................................. A61C 13/00
(52) U.S. Cl. .......................................................... 433/199.1
(58) Field of Search ........................................... 433/199.1

(56) References Cited

U.S. PATENT DOCUMENTS

| | | | |
|---|---|---|---|
| 606,198 | * | 6/1898 | Evans ................................. 433/199.1 |
| 1,945,767 | * | 2/1934 | Bergerhausen et al. .......... 433/199.1 |
| 2,418,833 | * | 4/1947 | Harris et al. ...................... 433/199.1 |
| 2,551,812 | | 5/1951 | Nelson .................................. 18/55.1 |
| 4,360,344 | * | 11/1982 | Colpitts ............................. 433/199.1 |
| 4,661,065 | * | 4/1987 | Gentleman et al. .............. 433/199.1 |
| 4,828,493 | * | 5/1989 | Nambu et al. .................... 433/199.1 |

FOREIGN PATENT DOCUMENTS

| | | |
|---|---|---|
| 2 090 395 | 1/1972 | (FR) . |
| 2 624 370 | 6/1989 | (FR) . |
| WO 89/04640 | 6/1989 | (WO) . |
| WO 91/11153 | 8/1991 | (WO) . |
| WO 94/08783 | 4/1994 | (WO) . |

* cited by examiner

Primary Examiner—Todd E. Manahan
(74) Attorney, Agent, or Firm—Foley & Lardner

(57) ABSTRACT

A stratified material (S, S') for a support part for dental prosthetic element or prosthesis comprising at least one first layer (5) of a fibrous tissue that is hardenable or has been already crosslinked or optionally hardened previously, or impregnated with crosslinked agents or synthetic material is connected at least partially and at least on one side to a second layer (4) of a rigid or soft material, for instance a synthetic material or silicone. The material is moldable and can be adapted specially to the model of a maxillary (1), a duplicate of a maxillary model or a maxillary. In the supporting body including such a stratified material, the second layer (4) is placed on the side facing the maxillary.

19 Claims, 3 Drawing Sheets

STRATIFIED MATERIALS USED IN DENTAL PROSTHESES

FIELD OF THE INVENTION

The present invention relates to a stratified material for support parts for dental prostheses and to a method for the production of such support.

BACKGROUND OF THE INVENTION

In the context of the invention, dental prostheses are to be understood as meaning all possible forms of dentures, such as prostheses or prosthetic elements as dentures in partly toothed or toothless jaws, as well as artificial teeth, crowns and bridge elements. Fixed prostheses or prosthetic elements are understood as meaning technical dental aids which consist of at least two artificial teeth connected to one another (including the necessary supporting or otherwise functional elements), such elements maintaining their mutual position and distance after removal from the jaw position.

The prostheses or prosthetic elements can—after prior adaptation by appropriately trained technical personnel (dentist, etc.)—either be inserted into the mouth or removed therefrom by the prosthesis wearer himself in a simple manner or be fastened indirectly or directly to the jaw in such a way that they can only be inserted or removed by said technical personnel. The prosthesis may rest on the oral mucous membrane, on residual teeth and/or on dental elements. For fastening or stabilization of the prosthesis, various dental measures or elements can be provided.

A prosthetic part generally consists of artificial teeth which are connected to a support base directly resting on the jaw covered with mucous membrane or which are mounted on the support base. The artificial teeth are usually tooth-colored and, like the support base, which as a rule consists of gum-colored plastic, have a functional and an aesthetic or cosmetic function. For reinforcement, reduction of fractures, stabilization or holding of dental elements or for corresponding reasons, an additional reinforcement may be necessary for the dental prosthesis. The reinforcing framework serving as a support part may be present in prefabricated form or prepared specially for an individual prosthesis, and this framework is as a rule incorporated by polymerization during the production of the dental prosthesis. However, in specific cases, the framework may also be incorporated subsequently into a hardened prosthetic part.

Reinforcements commonly used today are generally in the form of metal frameworks which either rest on the mucous membrane and/or are partly or wholly integrated in the prosthetic part. Various metals or alloys and different production processes are available for the production of these metal frameworks. Although metal frameworks produced in this manner can achieve very high strength and dimensional stability, they have various disadvantages both with respect to application and with respect to production.

Thus, the use of a metal in an aqueous, oral medium which is variously acidic or alkaline depending on eating habits and/or personal disposition give rise in principle to a problem if other metals are also simultaneously used in the oral cavity (for example other dental aids, such as, for example, fastening elements for the prosthesis, etc.). Owing to the different positions of two different metals in the electrochemical series, the saliva, acting as an electrolyte, results in the formation of corrosion currents, and the parts of the less noble metal go into solution. Consequently, the risk of intolerance, which is not inconsiderable owing to the incorporation of metals (especially the metals of subgroup V or VIII), may be increased.

In addition to the danger of biointolerance, metal frameworks for reinforcing dental prostheses give rise to an aesthetic problem since they shimmer through metallically in the case of a thin plastic veneer present, for example, because of space requirements, disturbing the visual impression particularly in anterior regions.

In addition to the metal reinforcing frameworks commonly used today, applications and methods in dental prosthetics are known in which different fiber materials are used for reinforcing the plastics part. Such applications and methods are described, for example, in EP-B1-0230 394, WO 91/11153 or U.S. Pat. No. 5,425,640. Substantially lighter prostheses permanently connected to the support framework can be realized by these methods. The fibers used (polyethylene, aramid and other fibers) are placed however, in a manner just as complicated as that described above, in mechanically shaped cavities in the plastics part of the dental prosthesis and then connected thereto chemically.

The shaping of a support part for a dental prosthesis is generally effected directly on a working model or on a model produced by duplication, in order to adapt it to the desired, individual structure of the prosthesis. When glass fibers or other abrasive fibers are used, it is necessary—as when metallic framework parts are used—to ensure that measures for maintaining the distance of the support part from the gum are taken in order to avoid injuries to the gum or to ensure sufficient comfort during wearing. Usually, in the production of the support part, an intermediate member independent thereof is provided for this purpose between model and fiber layer for maintaining the distance, so that the finished support part subsequently does not rest directly on the gum. Although the risk of injury to the gum is reduced in this way and the comfort during wearing may be improved, on the other hand the introduction and trapping of food residues are possible. Furthermore, two production steps essentially independent of one another have to be tailored to one another during the production of the support part. If corrections subsequently have to be made to such a support part, tearing of and damage to the fiber fabric may occur if, for example, too tight a fit is to be corrected by subsequent grinding.

SUMMARY OF THE INVENTION

It is the object of the present invention to overcome the problems associated with the prior art, which is permitted by providing a stratified material for support parts for dental prostheses and prostheses elements, support parts, and a method for making support parts. The stratified material includes at least one first layer of a hardenable or hardened material, which includes fibers of a different length which are impregnated with crosslinking agent(s) and/or with plastic, in braided, crossed or otherwise woven or knitted form to form a fiber fabric; and a second layer of soft, shapeable material, wherein the first layer is at least partly connected on one side to at least a part of the second layer.

Figure 1A:
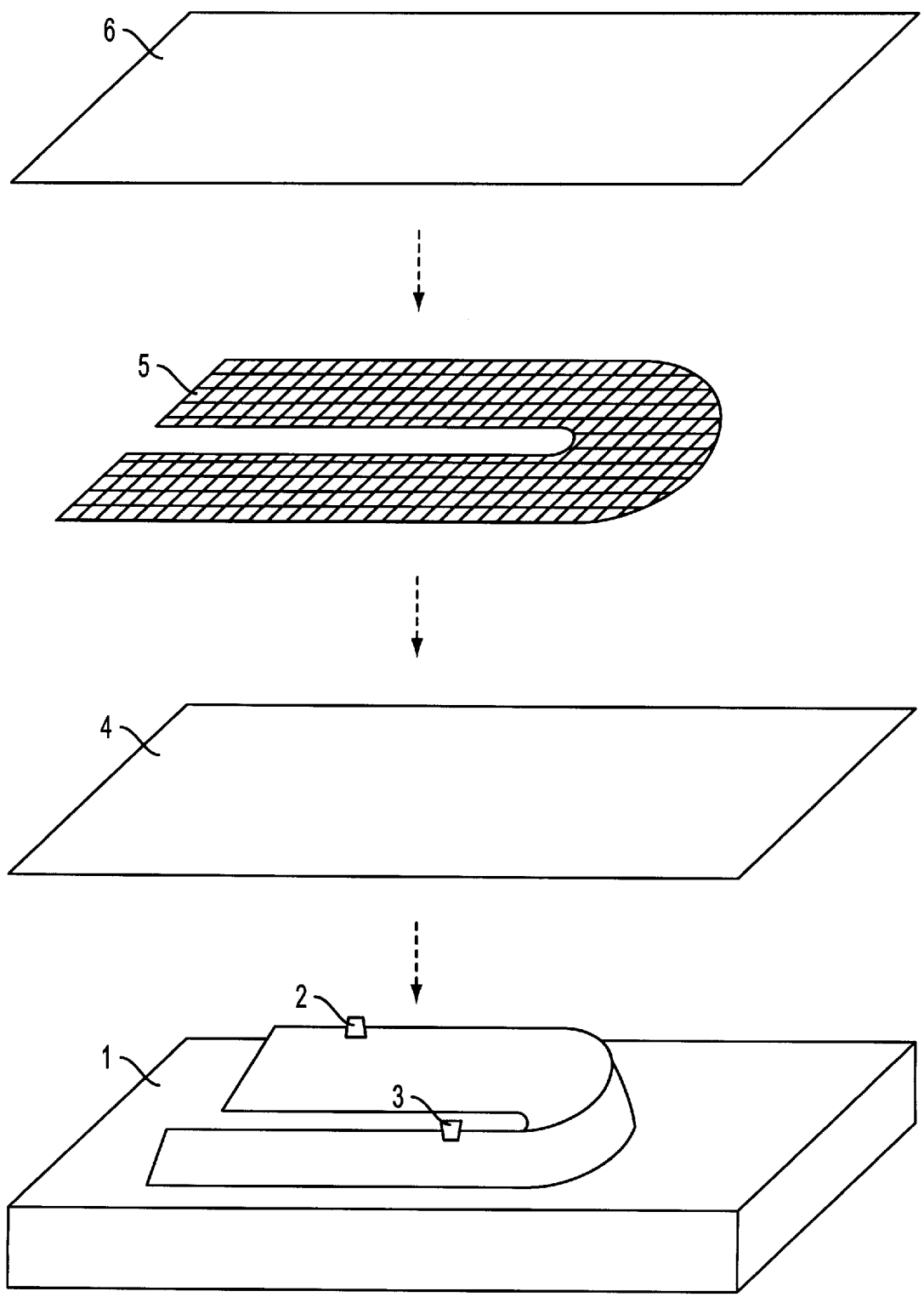
FIGS. 1a and 1b show possible sequences of the production of a support part according to the invention, as a base for a prosthesis.

Starting materials for the "base layer", the first layer of the stratified material, from which the support part according to the invention has been formed or will be formed may be fiberglass, aramid, PE, i-c and other fibers of different lengths, in braided, crossed or otherwise woven or knitted form. For example, fiber fabric impregnated with crosslinking agents or with precrosslinked plastic can be used for this purpose and said fabrics can be prefabricated in different forms tailored to the respective intended use for example (rectangular form, ellipsoidal form, the form of half an oval, and horseshoe-shaped) forms. This first layer can also comprise as a plurality of fiber layers, and "one layer" in the context of the invention is to be understood as meaning a layer which may also be multi-stratum, as long as it consists of the same material. This first layer is now provided—at least on one side, and in particular on the side which is to face the jaw region. A further, second layer which consists of rigid material or material which remains soft, such as, for example, the material sold by the company Myerson, Harrow, Middlesex, Great Britain, under the name "Soft Denture Liner". Such a material is distinguished by the fact that it remains soft, yields under pressure and has a specific resilience. Such materials are used as a permanently soft liner for prostheses. Below, the term "soft" for the material of the second layer is to be understood as meaning such a material. If it rests directly on the jaw, the result is improved comfort during wear. Furthermore, the adaptation of the prosthesis to the maxillary situation is facilitated since it adapts to a certain extent to the shape of the jaw and can act as a damping cushion when worn. If the second layer is formed from rigid material, this formation may be of interest for bridge structures or other prostheses which, for example, either do not rest directly on the jaw or in which a high degree of comfort during wear plays a minor role. Moreover, corrections which necessitate subsequent grinding of the already shaped support part from the basal side are possible here without damaging the fiber layer since they can be carried out in the second layer.

Although the second layer may have the same dimensions as the first layer and may be present fully as a double layer together with the latter, the layer material functions in the same way for certain applications if the second layer also only partly covers the first layer.

A support part having such a layer material permits the preparation of complete dental prostheses for toothless jaws, of partial dental prostheses for partly toothed jaws (partial edentulousness), of dental prostheses over holding, retention or anchoring elements or of implants in removable or screwed form.

If dental prostheses or prosthetic elements—in particular fixed ones—are mounted on such a support part, this results in good and permanently strong chemical bondability of the fiber reinforcement with the dental plastics used (e.g. PMMA [polymethyl methacrylate]), other possibilities, in addition to the above advantages relating to the maintenance of distance and the comfort during wear may be obtained. Consequently, complete filling of the distance from the base to the artificial teeth is thus possible, and the second layer can therefore be used for gum design. If the support part is additionally covered on the oral side with a third layer, the covering, preferably includes particular dental plastic, then the dental position and the vertical dimension of occlusion in the preparation of full dentures can thus be fixed by means of this layer in a particularly rational manner with processing in the patient's mouth, and the artificial teeth can be introduced into said layer.

The production of a dental prosthesis can be effected in various ways optimized for the respective intended use. The support part can be adapted to the anatomical shape of the jaw and can be given a geometry and dimension similar to the total prosthesis or its parts through the shapeability present. The support part can either be used in already processed and polymerized form for further build-up of the prosthesis or can be processed in a still unpolymerized or prepolymerized and hence individually shapeable state. Also, the support part can be used in a completely or finally polymerized (i.e. hardened) state only before or during preparation of the prosthesis.

The production of the support part is optionally effected directly on the working model or on a model produced by duplication, in accordance with the individual structures of the prosthesis, or, as already mentioned further above, directly in the patient's mouth by adaptation of the shape. The latter is possible because of the use of a layer material according to the invention for the support part, since irritation, which may occur as a result of direct skin contact with known fiber layer materials, can be suppressed by providing the second layer, which is preferably also to be arranged orally.

Such support parts may be prefabricated and optionally present in a modular form, easily and quickly usable for most requirements, and they may be colorless and translucent, tooth-colored, gum-colored or colored in any desired combination. Even in critical cases (e.g. thin overall thickness in anterior parts), a visually appealing design is also possible. Here too, the use of completely polymerized or only prepolymerized elements is possible, the latter being subsequently plastically formed in the laboratory and/or completely polymerized only after installation in the prosthesis.

Prefabricated fiberglass elements can thus advantageously be provided with a basally mounted plastics base. On the model, it is then only necessary to form the parts which are on top or anterior and posterior parts.

Prosthetic elements having such support parts can also be connected to support parts produced in another manner, for example those having a metal framework as in traditionally produced prosthetic elements, in particular in cases where metallic reinforcing frameworks cannot be dispensed with. Thus, for example, the anterior parts of partial dental prostheses (such as, for example, cast prostheses) for partially toothed jaws (partial edentulousness) can be formed by prosthetic elements which have support parts according to the invention. Instead of an aesthetically disturbing, metallic reinforcement, the support may be gum-colored or tooth-colored plastic in any desired color adaptation, while the posterior parts are still in the form of a metal framework. Even where, for space reasons or other reasons, facing of metallic retaining elements mounted on the tooth base is dispensed with, a facing supported by the support part according to the invention can be applied owing to the small space requirement and the easy shapeability of said support part. The support part of these prosthetic elements can be connected to the now smaller and therefore lighter metal framework by mechanical retention or in a chemical manner.

The invention is described below purely by way of example with reference to drawings.

FIG. 1a shows a possible sequence for the production of a support part for a prosthesis. A layer, referred to below as second layer 4, is applied to a model 1 of an edentulous jaw or jaw provided with individual teeth 2 or artificial fixing points 3. This second layer 4 may consist of a hard or soft material or of a combination thereof, of—optionally dental—plastic or of a material such as silicone. The thickness of the layer should be chosen according to the respective intended use, as should the area thereof. A further layer, referred to below as first layer 5, is applied on top. This may consist, for example, of a mat, the mat being reinforced by glass fibers or other fibers, multilayer or precrosslinked with dental plastic, plastic-ceramic composites or similar material. In general, this first layer is not yet completely polymerized and is still shapeable.

Figure 1B:
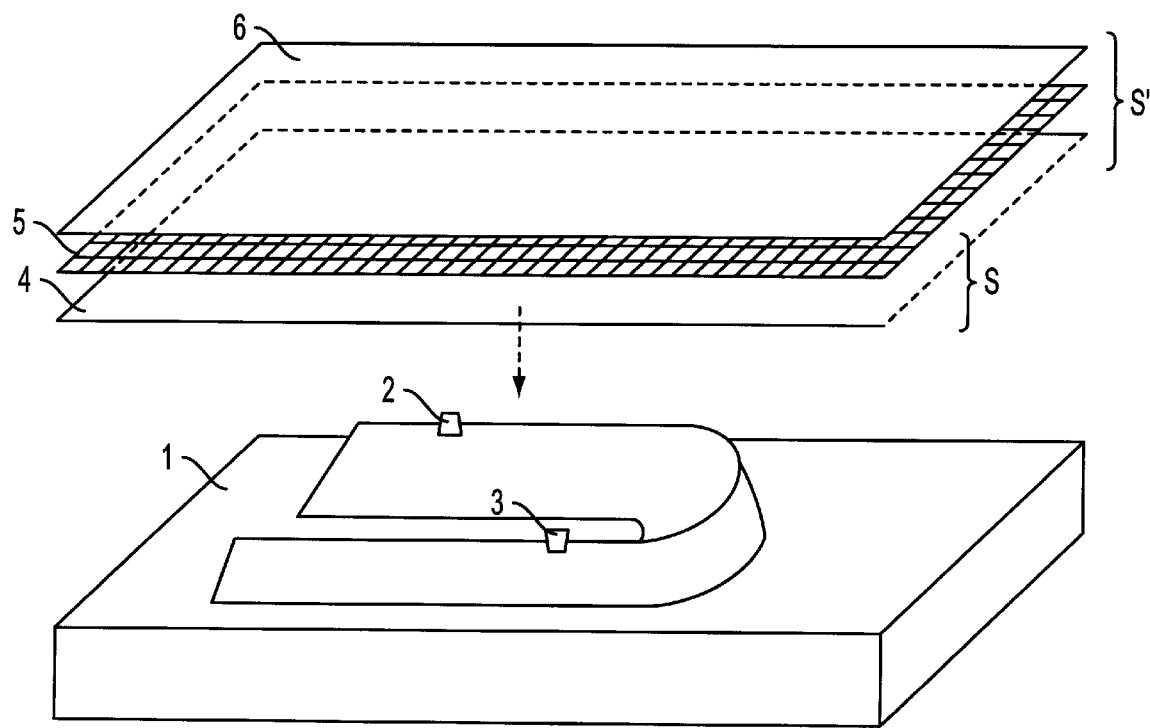

As shown in FIG. 1b, first and second layer 4 and 5 may be bonded to one another as layer material S—prior to being applied—to the model, and layer materials can be adapted to the contours of the model 1.

After adaptation and any cutting to size of the two layers 4 and 5, which is optionally effected for each of the two layers, particularly when present together as layer material S, this basic structure for the support part 45 is hardened; if necessary, further shape corrections (for example by subsequent grinding) are made. The support part produced in this manner can then be provided completely or only orally with a plastics covering 6. The other parts of the prosthesis can be mounted thereon in a known manner and completed.

As in the case of the two layers 4 and 5, this covering 6 can however also be bonded to said layers as layer material S', and this can be shaped and subsequently hardened in a single production step on the model 1 or in the patient's mouth, as shown in FIG. 1b.

Thus, a support part according to the invention can be shaped and hardened both stepwise (for example, second layer 4 of plastic as spacer, first layer 5, as multi-stratum fiber layer, covering 6 of plastic) on the model and in a single operation in which a layer material S' comprising second layer 4, first layer 5 and covering 6 is optionally preshaped, completely adapted and hardened.

Figure 2:
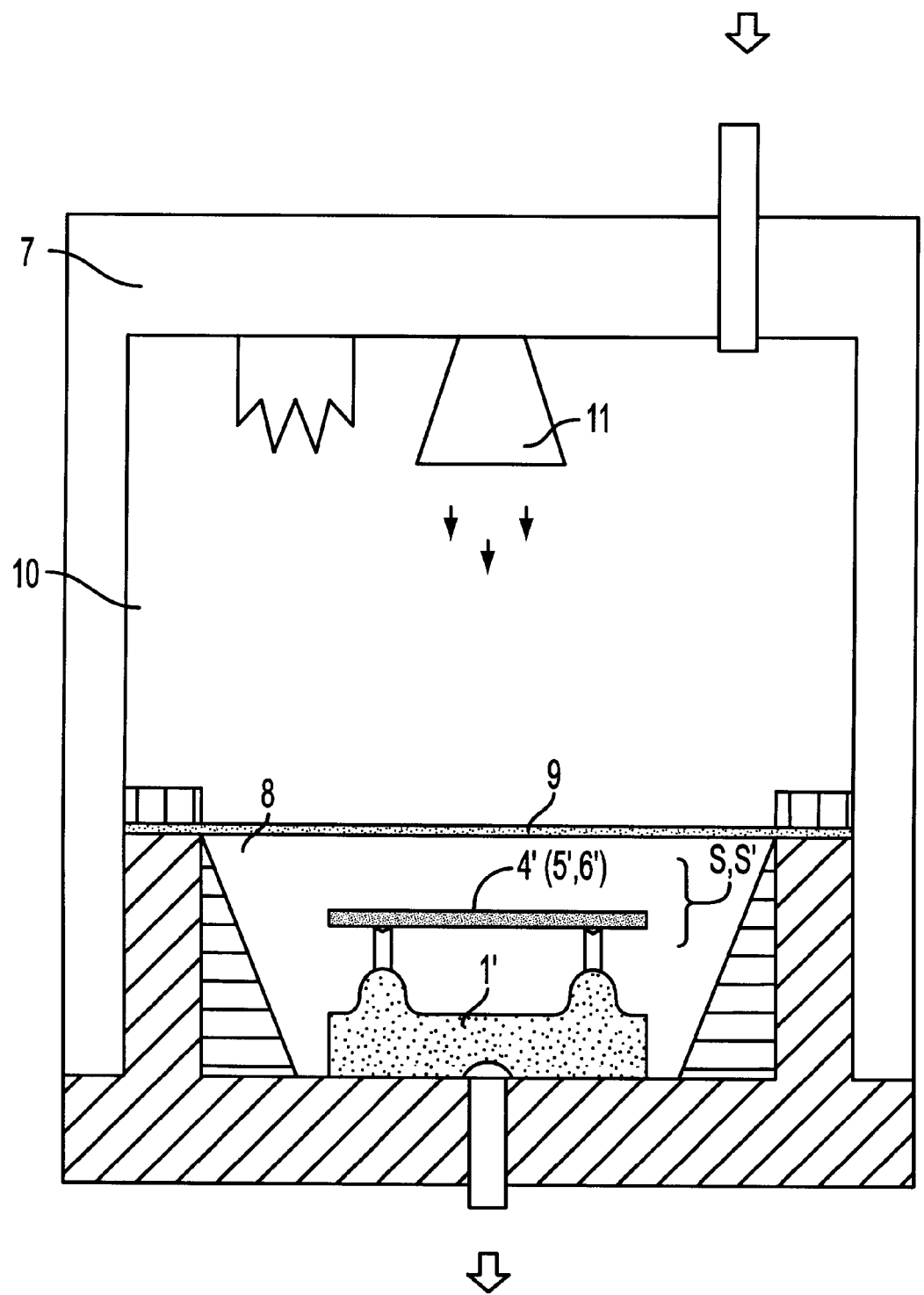
FIG. 2 shows an adapting and hardening apparatus for the production of the base.

As shown in FIG. 2, this can be effected in a semiautomatic manner if, after application of a second layer 4' (serving as a spacer and comprising a sheet suitably cut to size and composed of, for example, dental plastic,) the model 1' is placed in an apparatus 7 by applying a vacuum on side 8 of a flexible membrane film 9 dividing apparatus 7 which faces the model and/or by generating of excess pressure on side 10 of membrane film 9 which faces away from the model, said membrane film 9 presses the plastic in an interlocking manner against the maxillary model, after which. Afterwards the cast thus produced is prehardened or completely hardened by suitable irradiation means 11 or by pressure, heat or autopolymerization or by a combination of said treatments, inside or outside the apparatus.

The first layer 5' of fiber fabric is then applied in a similar manner, adapted to the model over the second layer (spacer) 4' and prehardened or completely hardened. The final application of the covering 6' can be effected analogously to the preceding steps. If the individual layers are only prehardened, the total structure can then be completely hardened in a final step. A single operation is possible in such a manner when a layer material S (S') already consisting of at least the two layers 4' and 5' and optionally also already comprising the covering 6' is shaped and hardened in this apparatus 7.

Prefabricated support parts as a prosthesis base for various applications may be present as modular parts without a covering; the covering can be applied subsequently together with the corresponding individual prosthesis superstructures by the respective dental laboratory.

Instead of the use of excess pressure and/or a vacuum, in a simpler variant of the method the sheets of plastic or fiber fabric can be pressed against the model by a suitable plastic mass (for example silicone). This can also be effected directly in the mouth in a corresponding manner. However, under certain circumstances, this may lead to a slightly less exact formation of the impression.

Figure 3:
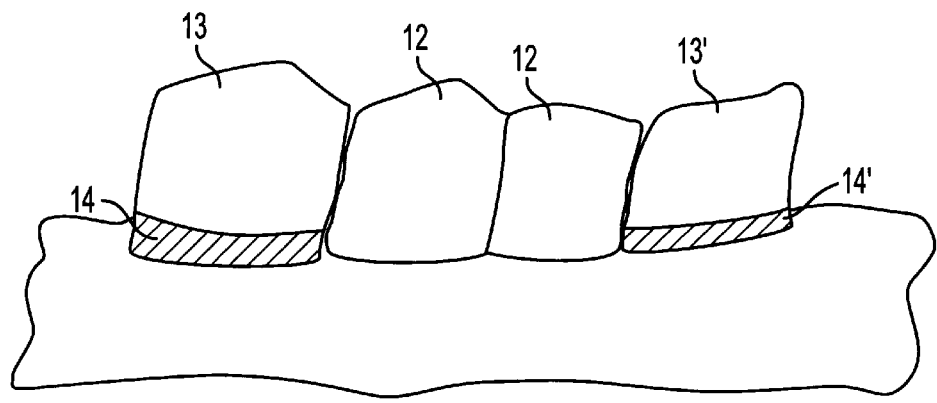
FIG. 3 shows a prosthesis for partial edentulousness with abutment teeth.

In a basically similar manner, both complete prostheses, as shown by way of example in FIG. 1, and partially edentulous prostheses 12 for partially toothed jaws, as shown by way of example in FIG. 3, can be produced. Such a partially edentulous prosthesis 12 can be fixed, for example, between two abutment teeth 13, 13' on which, if required, metal cribs 14, 14' for fastening a posterior anchor (not visible in the Figure) can be mounted on the tooth base.

What is claimed is:

1. A stratified material for support parts for dental prostheses and prosthetic elements comprising:

at least one first support layer of a hardenable or hardened material, which includes fibers of a different length which are impregnated with crosslinking agent(s) and/or with plastic, in braided, crossed or otherwise woven or knitted form to form a fiber fabric; and a second layer of soft, shapeable material, wherein the first layer is at least partly connected on one side to at least a part of the second layer.

2. A stratified material according to claim 1, wherein the second layer comprises plastic or silicone.

3. A stratified material as claimed in claim 1, wherein the stratified material is shapeable on a duplicate of a maxillary model or on a jaw.

4. A stratified material as claimed in claim 1, wherein the fiber fabric of the first layer is precrosslinked with dental plastic or with a plastic-ceramic composite.

5. A stratified material for support parts for dental prostheses and prosthetic elements comprising:

at least one first support layer of an already hardened fiber fabric impregnated with crosslinking agent(s), or plastic, or a fiber composite; and a second layer of soft, shapeable material, wherein the first layer is at least partly connected on one side to at least a part of the second layer.

6. A stratified material according to claim 5, wherein the second layer comprises plastic or silicone.

7. A support part for dental prostheses and prosthetic elements comprising, a stratified material which comprises at least one first support layer of a hardenable or hardened material, which includes fibers of a different length which are impregnated with crosslinking agent(s) and/or with plastic, in braided, crossed or otherwise woven or knitted form to form a fiber fabric, and a second layer of soft, shapeable material, wherein the first layer is at least partly connected on one side to at least a part of the second layer, and wherein the second layer is arranged on the side which faces the jaw.

8. A support part as claimed in claim 7, wherein the first layer is covered at least on the oral side with a covering which includes dental plastic.

9. A support part as claimed in claim 7 which is preshaped.

10. A support part as claimed in claim 7 which is subsequently shapeable.

11. A denture, prosthesis or prosthetic element comprising a support part which comprises a stratified material, which comprises at least one first support layer of a hardenable or hardened material, which includes fibers of a different length which are impregnated with crosslinking agent(s) and/or with plastic, in braided, crossed or otherwise woven or knitted form to form a fiber fabric, and a second layer of soft, shapeable material formed as a distance filler, wherein the first layer is at least partly connected on one side to at least a part of the second layer, and wherein the second layer is arranged on the side which faces the jaw.

12. A denture, prosthesis or prosthetic element as claimed in claim 11, wherein the denture, prosthesis or prosthetic element is fixed.

13. A method for the production of a support part for dental prostheses and prosthetic elements, which support part comprises a stratified material comprising at least one first support layer of a hardenable or hardened material, which includes fibers of a different length which are impregnated with crosslinking agent(s) and/or with plastic, in braided, crossed or otherwise woven or knitted form to form a fiber fabric, and a second layer of soft, shapeable material, wherein the first layer is at least partly connected on one side to at least a part of the second layer, and wherein the second layer is arranged on the side which faces the jaw;

wherein the method comprises:

applying the second layer as a spacer or distance filler to a model or duplicate of a model of a jaw or maxillary section or to the jaw itself; and applying the first layer on the second layer; and shaping and stabilizing the first layer according to the contours of the model or of the jaw.

14. A method as claimed in claim 13, wherein the shaping and stabilizing is carried out with the second layer.

15. A method as claimed in claim 13, wherein the second layer includes a dental plastic and is permanently bonded to the first layer.

16. A method as claimed in claim 13, wherein the first layer, with the exception of areas which, if required, are connected directly to one or more other support parts, is provided at least on the oral side with a covering of plastic.

17. A method as claimed in claim 16, wherein all sides of the first layer are provided with a covering of plastic.

18. A method as claimed in claim 13, wherein the second layer comprises plastic or silicone, optionally in the form of individual layer pieces, and serves as a distance filler.

19. A method for the production of a support part for dental prostheses and prosthetic elements comprising a stratified material, which stratified material comprises at least one first support layer of a hardenable or hardened material, which includes fibers of a different length which are impregnated with crosslinking agent(s) and/or with plastic, in braided, crossed or otherwise woven or knitted form to form a fiber fabric, and a second layer of soft, shapeable material, wherein the first layer is connected at least on one side at least partly to the second layer, and wherein the second layer is arranged on the side which faces the jaw, wherein the method comprises:

applying the stratified material to a model or a duplicate of a model of a jaw or maxillary section, or on the jaw itself; and shaping and stabilizing the stratified material according to the contours of the model or of the jaw.

* * * * *